(12) United States Patent
Lerebours-Pegeonniere et al.

(10) Patent No.: US 8,217,030 B2
(45) Date of Patent: Jul. 10, 2012

(54) ASSOCIATION OF A SINUS NODE IF CURRENT INHIBITOR AND A BETA BLOCKER

(75) Inventors: Guy Lerebours-Pegeonniere, Levallois-Perret (FR); Jean-Henri Calvet, Paris (FR)

(73) Assignee: Les Laboratoires Servier, Suresnes Cedex (FR)

( * ) Notice: Subject to any disclaimer, the term of this patent is extended or adjusted under 35 U.S.C. 154(b) by 633 days.

(21) Appl. No.: 12/378,080

(22) Filed: Feb. 11, 2009

(65) Prior Publication Data

US 2009/0209515 A1 Aug. 20, 2009

(30) Foreign Application Priority Data

Feb. 14, 2008 (FR) ..................... 08 00800

(51) Int. Cl.
*A01N 43/00* (2006.01)
*A61K 31/55* (2006.01)
*C07D 223/16* (2006.01)
(52) U.S. Cl. ............... 514/212.04; 514/217.01; 540/594
(58) Field of Classification Search ............. 514/212.04, 514/217.01; 540/594
See application file for complete search history.

(56) References Cited

U.S. PATENT DOCUMENTS

2004/0242565 A1* 12/2004 Toshima et al. ............... 514/218
2007/0142356 A1* 6/2007 Benatar et al. ........... 514/212.07

FOREIGN PATENT DOCUMENTS

| EP | 1362590 | 11/2003 |
|---|---|---|
| EP | 1800678 | 6/2007 |
| EP | 1800683 | 6/2007 |

OTHER PUBLICATIONS

De Diviths et al. European Heart Journal, 1987, vol. 8, Suppl. M, abstract.*
Zewail et al. Tex Heart Inst J 2003;30:109-113.*
Lechat, et al, "De l'ischemie a l'insuffisance cardiaque: la frequence cardiaque—acteur ou marqueur" Therapie, vol. 59, No. 5, p. 485-489, Sep. 2004.
The Beautiful Study Group, "The Beautiful study: Randomized trial of ivabradine in patients with stable coronary artery disease and left ventricular systolic dysfunction—baseline characteristics of the study population" Cardiology, vol. 110, No. 4, p. 271-282, 2008.
L. Mangin, et al., "relationships between heart rate and heart rate variability: Study in conscious rats" Journal of Cardiovascular Pharmacology, vol. 32, p. 601-607, 1998.
French Preliminary Search Report for FR0800800 of Aug. 7, 2008.
Amosova, et al.; JACC, 2010, 55, Abstract.
Sulfi, et al., Int. J. Clin. Pract., 2006, 60, 222-228.

* cited by examiner

*Primary Examiner* — Samira Jean-Louis
(74) *Attorney, Agent, or Firm* — Hueschen and Sage

(57) ABSTRACT

Association of a sinus node If current inhibitor and a β-blocker and also pharmaceutical compositions containing it.

Medicinal products containing the same which are useful in treating angina pectoris, ischaemia, and heart failure.

8 Claims, No Drawings

ASSOCIATION OF A SINUS NODE IF CURRENT INHIBITOR AND A BETA BLOCKER

The present invention relates to the fixed association of a sinus node If current inhibitor and a beta blocker, or β-blocker, and also to pharmaceutical compositions containing them.

More specifically, the present invention relates to a fixed association of a sinus node If current inhibitor which is ivabradine, or 3-{3-[{[(7S)-3,4-dimethoxybicyclo[4.2.0]octa-1,3,5-trien-7-yl]methyl}(methyl)amino]propyl}-7,8-dimethoxy-1,3,4,5-tetrahydro-2H-3-benzazepin-2-one, of formula (I):

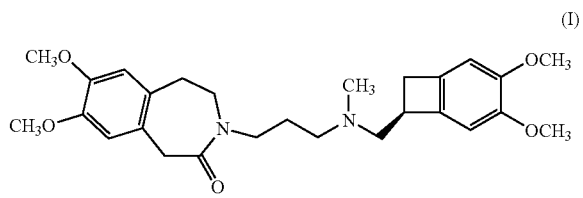

or one of its hydrates, crystalline forms or addition salts of any thereof with a pharmaceutically acceptable acid, and a β-blocker.

The present invention relates preferably to a fixed association between a β-blocker of the cardioselective type, more especially atenolol or one of its hydrates, crystalline forms or addition salts of any thereof with a pharmaceutically acceptable acid, and, as sinus node If current inhibitor, ivabradine hydrochloride or one of its hydrates or crystalline forms.

Sinus node If current inhibitors, more especially ivabradine and its hydrates and crystalline forms and addition salts thereof with a pharmaceutically acceptable acid, more especially its hydrochloride, have very valuable pharmacological and therapeutic properties, especially negative chronotropic properties (lowering of heart rate), which make these compounds useful in the treatment or prevention of various clinical situations of myocardial ischaemia such as angina pectoris, myocardial infarct and associated rhythm disturbances, and also in various pathologies involving rhythm disturbances, especially supraventricular rhythm disturbances, and in heart failure.

The preparation and therapeutic use of ivabradine and addition salts thereof with a pharmaceutically acceptable acid, more especially its hydrochloride, have been described in the European patent specification EP 0 534 859.

β-blockers, or β-blocking agents, are compounds which inhibit β-adrenergic receptors. β-blockers have the effect of slowing down the heart by decreasing the slope of depolarisation, reducing the heart's workload and reducing its oxygen demands. Consequently, β-blockers are used in the treatment of angina, especially in the prevention of attacks. In apparently paradoxical manner, β-blockers are used in the treatment of heart failure.

The β-blockers according to the invention are, preferably, cardioselective β-blockers, that is to say they preferentially block β1 cardiac receptors. Their cardioselective character makes it possible to reduce secondary effects, especially peripheral vasoconstriction and bronchoconstriction. The cardioselective β-blockers are more especially selected from the following list: acebutolol, atenolol, betaxolol, bisoprolol, esmolol, metoprolol and nebivolol.

The literature and the opinion leaders in the field of cardiovascular disorders generally conclude that it is difficult to demonstrate the superiority of associations comprising a β-blocker plus another class of anti-angina compounds over β-blocker monotherapy in the treatment of stable angina.

The present invention demonstrates, surprisingly, that sinus node If current inhibitors and, more especially, ivabradine are capable of potentiating the effects of β-blockers on increasing exercise capacity. Accordingly, this increasing of exercise capacity is related to a synergy between the active ingredients, i.e. a sinus node If current inhibitor and a β-blocker.

In the pharmaceutical compositions according to the invention, the amounts of sinus node If current inhibitor and of β-blocker are matched to the nature of those active ingredients and their relative proportions are accordingly variable as a function of said active ingredients.

The pharmaceutical compositions according to the invention have proportions of from 1.6% to 80% of the total weight of the active ingredients for the sinus node If current inhibitor and from 20% to 98% of the total weight of the active ingredients for the β-blocker.

When the sinus node If current inhibitor is ivabradine in hydrochloride salt form and the β-blocker is atenolol, the preferred percentages for that association are around 25% ivabradine in hydrochloride salt form as opposed to 75% atenolol.

The present invention relates also to pharmaceutical compositions comprising, as active ingredient, an association of a sinus node If current inhibitor and a β-blocker, optionally in the form of pharmaceutically acceptable salts, on their own or together with one or more appropriate, inert, non-toxic carriers or excipients.

In the pharmaceutical compositions according to the invention, the weight proportion of active ingredients (weight of active ingredients over total weight of the composition) is advantageously from 5 to 50%.

As regards the pharmaceutically acceptable excipients, there may be mentioned, without implying any limitation, binders, diluents, disintegrating agents, stabilisers, preservatives, lubricants, fragrances, aromas or sweeteners.

By way of non-limiting example there may be mentioned:
- as diluents: lactose, dextrose, sucrose, mannitol, sorbitol, cellulose, glycerol;
- as lubricants: silica, talc, stearic acid and its magnesium and calcium salts, polyethylene glycol;
- as binders: aluminium and magnesium silicate, starch, gelatin, tragacanth, methylcellulose, sodium carboxymethylcellulose and polyvinylpyrrolidone.

Among the pharmaceutical compositions according to the invention, there will be more especially selected those that are suitable for administration by the oral, parenteral and especially intravenous, per- or trans-cutaneous, nasal, rectal, perlingual, ocular or respiratory routes, more specifically tablets or dragées, sublingual tablets, hard gelatin capsules, glossettes, capsules, lozenges, injectable preparations, aerosols, eye drops, nose drops, suppositories, creams, ointments or dermal gels.

The preferred route of administration is the oral route and the corresponding pharmaceutical compositions may allow instantaneous or deferred release of the active ingredients.

Preferred pharmaceutical compositions are tablets.

The dosage can be varied according to the nature and severity of the disorder, the administration route and also the age and weight of the patient. In the compositions according to the invention it ranges from 25 to 150 mg for the β-blocker and from 2.5 to 30 mg of sinus node If current inhibitor per 24 hours in one or more administrations. Preferably, when the sinus node If current inhibitor is ivabradine, the administration dose is from 5 to 7.5 mg twice per day (b.i.d.). When the β-blocker is atenolol, the daily administration dose is preferably 50 mg in one administration.

Finally, the pharmaceutical compositions according to the invention are useful in the manufacture of medicaments intended for the treatment of angina pectoris, ischaemia and heart failure.

The examples of compositions hereinbelow are given by way of non-limiting example.

Ivabradine/Atenolol Tablets:

EXAMPLE 1

| Constituents | Amount (mg) |
| --- | --- |
| ivabradine hydrochloride | 5 |
| atenolol | 50 |
| hydrophobic colloidal silica | 0.4 |
| starch | 6 |
| magnesium stearate | 2 |
| microcrystalline cellulose | 50 |
| lactose | 86.6 |
| For a tablet totalling | 200 |

EXAMPLE 2

| Constituents | Amount (mg) |
| --- | --- |
| ivabradine hydrochloride | 7.5 |
| atenolol | 50 |
| hydrophobic colloidal silica | 0.4 |
| starch | 6 |
| magnesium stearate | 2 |
| microcrystalline cellulose | 50 |
| lactose | 84.1 |
| For a tablet totalling | 200 |

Clinical Study

The patients selected for this clinical study are men and women from 18 to 75 years of age who have suffered from angina pectoris for at least 3 months and been treated with β-blockers such as atenolol (50 mg o.d.) or any other β-blocker at an equivalent dose for at least 3 months. These patients have, despite their treatment, a positive exercise tolerance test (ETT) and daily symptoms of angina pectoris.

This double-blind, parallel-group, international clinical study was carried out in 889 patients. The patients, all of whom are receiving atenolol, are randomised into two groups:
- in addition to the β-blocker, the first group is given ivabradine (hydrochloride) at a dose of 5 mg twice a day for two months and then at a dose of 7.5 mg twice a day for a further two months;
- in addition to the β-blocker, the second group is given a placebo for 4 months.

The patients are subjected to a treadmill exercise tolerance test (ETT) in accordance with the Bruce protocol before ivabradine is administered (that is when receiving β-blocker on its own), and after 4 months of treatment with the association between ivabradine and atenolol. The principal parameters measured in the course of the effort test are:
- total exercise duration (TED)—the TED includes the time taken for the treadmill to come to a stop or, that is, a duration of about 10 seconds starting from the patient's request to stop the exercise;
- the time until the "angina pectoris" pain forces the patient to stop the exercise (TLA);
- the time until the onset of the "angina pectoris" pain (TAO);
- the time taken for a 1 mm ST segment depression (TST) to appear on the electrocardiographic recording, this being a reflection of ischaemia and corresponding to the electrical sign of pain in the cardiac muscle.

These measurements are made at trough activity of the association of active ingredients or, that is, 12±1 hours and 24±2 hours after administration of the active ingredients.

The ivabradine/β-blocker association according to the invention ensures good acceptability and good safety of use according to the data from the compliance summary.

The patients have a mean age of 60±8 years. On entry into the study, the mean systolic/diastolic arterial pressure and heart rate of the patients at rest are respectively, on average: 127±12/78±7 mmHg and 67±7 beats per minute. After 4 months of treatment with the association, the heart rate has reduced by 9±10 bpm (β-blocker+placebo 1±10 bpm).

The mean improvements in the various parameters measured during the treadmill exercise test, between the value measured before the start of treatment with ivabradine and the end of the treatment period, are set out in the table below:

|  | β-blocker + ivabradine (n = 441) | β-blocker + placebo (n = 434) | p-value |
| --- | --- | --- | --- |
| TED | 24 ± 65 | 8 ± 64 | p < 0.001 |
| TAO | 49 ± 83 | 23 ± 79 | p < 0.001 |
| TLA | 26 ± 66 | 9 ± 64 | p < 0.001 |
| TST | 46 ± 93 | 15 ± 87 | p < 0.001 |

Improvements in parameters (in seconds, mean ± SD)

This study shows that ivabradine is capable of improving exercise tolerance in patients already receiving a standard dose of β-blockers.

The high level of compliance (99% in the patients receiving ivabradine) and the low percentage of serious adverse events show the acceptability and safety of the association of ivabradine plus β-blocker compared to the β-blocker in monotherapy.

The invention claimed is:

1. A composition comprising a combination of a sinus node If current inhibitor which is ivabradine, or 3-{3-[{[(7S)-3,4-dimethoxybicyclo[4.2.0]octa-1,3,5-trien-7-yl]methyl}-(methyl)amino]propyl}-7,8-dimethoxy-1,3,4,5-tetrahydro-2H-3-benzapenin-2-one, or one of its hydrates, crystalline forms or addition salts of any thereof with a pharmaceutically acceptable acid and a β-blocker.

2. The composition of claim 1, wherein the sinus node If current inhibitor is ivabradine-3-{3-[{[(7S)-3,4-dimethoxybicyclo[4.2.0]octa-1,3,5-trien-7-yl]methyl}(methyl)amino] propyl}-7,8-dimethoxy-1,3,4,5-tetrahydro-2H-3-benzazepin-2-one-hydrochloride or one of its hydrates or crystalline forms.

3. The composition of claim 1, wherein the β-blocker is a cardioselective β-blocker.

4. The composition of claim 1, wherein the β-blocker is atenolol or bisoprolol or one of its hydrates, crystalline forms or addition salts of any thereof with a pharmaceutically acceptable acid.

5. The composition of claim 1, wherein the composition comprises ivabradine, or one or its hydrates, crystalline forms or addition salts of any thereof with a pharmaceutically acceptable acid, and atenolol, or one of its hydrates, crystalline forms or addition salts of any thereof with a pharmaceutically acceptable acid.

6. A pharmaceutical composition comprising, as active ingredient, a composition of claim 1, alone or in combination with one or more pharmaceutically acceptable excipients.

7. A method of treating a living animal body, including a human, afflicted with a condition selected from angina pectoris, ischaemia, and heart failure, comprising the step of administering to the living animal body, including a human, a therapeutically effective amount of the composition of claim 1.

8. The composition of claim 1, wherein the composition comprises ivabradine, or one or its hydrates, crystalline forms or addition salts of any thereof with a pharmaceutically acceptable acid, and bisoprolol, or one of its hydrates, crystalline forms or addition salts of any thereof with a pharmaceutically acceptable acid.

* * * * *

UNITED STATES PATENT AND TRADEMARK OFFICE
CERTIFICATE OF CORRECTION

PATENT NO. : 8,217,030 B2  
APPLICATION NO. : 12/378080  
DATED : July 10, 2012  
INVENTOR(S) : Guy Lerebours-Pigeonniere and Jean-Henri Calvet Page 1 of 1

It is certified that error appears in the above-identified patent and that said Letters Patent is hereby corrected as shown below:

Title Page, Item (12) should read --Lerebours-Pigeonniere--.

Title Page, Inventors: "Guy Lerebours-Pegeonniere" should be --Guy Lerebours-Pigeonniere--.

Signed and Sealed this
Fourth Day of September, 2012

David J. Kappos
*Director of the United States Patent and Trademark Office*